United States Patent [19]

Mimms

[11] Patent Number: 5,254,458
[45] Date of Patent: Oct. 19, 1993

[54] IMMUNOASSAYS USING ANTIGENS PRODUCED IN HETEROLOGOUS ORGANISMS

[75] Inventor: Larry T. Mimms, Lake Villa, Ill.

[73] Assignee: Abbott Laboratories, Abbott Park, Ill.

[21] Appl. No.: 922,354

[22] Filed: Jul. 29, 1992

Related U.S. Application Data

[63] Continuation of Ser. No. 701,626, May 14, 1991, which is a continuation of Ser. No. 549,679, Jan. 5, 1990, which is a continuation of Ser. No. 115,135, Oct. 30, 1987.

[51] Int. Cl.$^5$ .............................. G01N 33/53
[52] U.S. Cl. ...................... 435/5; 435/7.94; 435/7.1; 435/7.92; 435/973; 435/974; 436/820
[58] Field of Search ............ 435/5, 7.1, 7.5, 7.92, 435/794, 973, 974; 436/820

[56] References Cited

U.S. PATENT DOCUMENTS 4,774,175  9/1988  Chang et al. .................... 435/5

FOREIGN PATENT DOCUMENTS 0199301  4/1986  European Pat. Off. .
0307149  3/1989  European Pat. Off. .

OTHER PUBLICATIONS

Odell et al: Principles of Competitive Protein–Binding Assays John Wiley & Sons, Inc. 1983, pp. 246–249.
Crowl, et al Cell 41, 979–986, 1985 (II).
Voller, et al In: Manual of Chemical Laboratory Immunology 3rd Edition, Editing: Rose, et al, 1986.

*Primary Examiner*—Christine M. Nucker
*Assistant Examiner*—Jeffrey Stucker
*Attorney, Agent, or Firm*—Priscilla E. Porembski

[57] ABSTRACT

This invention relates to improved "sandwich" immunoassays for antibodies in body fluids of the type where antigen specific for the antibody to be detected is disposed on a solid support and binds antibody from the body fluid, from which the antibody bound to the solid support is detected by a labeled antigen to the antibody to be detected. The improvement comprises using antigens from heterologous cell sources.

23 Claims, No Drawings

IMMUNOASSAYS USING ANTIGENS PRODUCED IN HETEROLOGOUS ORGANISMS

This application is a continuation of application Ser. No. 07/701,626, filed May 14, 1991 which is a continuation of application Ser. No. 07/549,679, filed Jul. 5, 1990, which is a continuation of application Ser. No. 115,535, filed Oct. 30, 1987.

BACKGROUND OF THE INVENTION

A. Field of the Invention

The present invention relates to a method of performing a sandwich type immunoassay for the detection of an antibody using a coated antigen and a labeled antigen, wherein the labeled antigen and the coated antigen are produced from genetically unrelated organisms ("heterologous species"). More particularly, the present invention relates to a solid phase method and device for detecting antibodies to some antigen ("X") in mammalian fluids or tissue wherein the antibody of interest is sandwiched between an antigen "X", which is bound to a solid phase, and an antigen "X" or a common epitope thereof, which is derived from a heterologous organism and bound to a label. The method and device of the present invention are useful in laboratory medicine because they permit a physician or veterinarian to determine rapidly and specifically whether a patient has an immune response to a particular organism or antigen, thereby reflecting present or prior exposure to that organism or antigen. In particular, the method and device of this invention is useful in rapidly and specifically detecting an immune response and thus exposure to the HTLV III virus which has been associated with acquired immune deficiency syndrome (AIDS).

B. Prior Art

Most immunoassays for detection of an antibody involve an antigen coated solid phase which is used to capture antibodies specific to the coated antigen. The captured antibodies are then quantitated and/or identified using an anti-antibody to which a detection system such as an enzymes or radioisotope is conjugated.

A second type of immunoassay also utilizes an antigen coated solid phase to capture antigen specific antibodies. However, unlike the first immunoassay above, the captured antibodies of the second type of immunoassay are quantitated and/or identified using an antigen cross-linked to a radiolabel or an enzyme which serves as a detection system. In this second type of immunoassay, both the antigen coating the bead and the antigen bearing the label are identical and from the same organism (source) and bear the same contaminants. Hereinafter, antigens which are obtained from the same or related species of organisms are referred to as "homologous" antigens.

For example, current immunoassays for the detection of antibodies to HTLV III (anti-HTLV III) require extensive specimen dilution; utilize virus purified from human cell line H9 to coat a solid phase; and finally, utilize a non-specific probe (e.g. Anti-human IgG, conjugated to horseradish peroxidase (HRPO)). In these immunoassays, biological fluids are screened for the presence of anti-HTLV III by contacting the unknown sample with a disrupted virus coated solid phase. Antibody to the HTLV III virus then binds to the virus coated solid phase. Because the disrupted virus produces a plurality of antigens, which are coated to the solid phase, any antibody in the sample, which is reactive against contaminants in the disrupted viral preparations, will also bind to the coated solid phase. Once antibody is bound to the solid phase, it will produce a significant number of "false positives" regardless of whether a labeled antibody (first type immunoassay) or a labeled homologous antigen (second type immunoassay) is used as the probe.

Accordingly, it is an object of the present invention to provide an immunoassay method and device for detecting and/or quantitating anti-HTLV III which has specificity, i.e., overcomes this "false positives" problem.

Unlike the immunoassays, competitive binding assays exist which overcome some of the specificity problems. For example, the competitive protein binding assay for anti-HTLV III uses recombinant antigens and allows discrimination between antibodies against HTLV III envelope (ENV) and HTLV III Core antigens. However, this procedure is lengthy, typically being carried out overnight. Moreover, it requires two solid phases i.e., beads coated with p41 envelope antigen and beads coated with p24 core antigen.

Accordingly, it is an object of the present invention to provide an immunoassay for anti-HTLV III which is not only rapid but which also has the specificity of a competitive binding assay without requiring two solid phases. cl SUMMARY OF THE INVENTION The present invention is directed to an improvement in the method of performing a sandwich immunoassay for detecting antibody to a specific antigen in a test sample wherein a first antigen specific to the antibody to be detected is immobilized on a solid phase, wherein the antibody to be detected in the test sample binds to the first antigen thereby becoming immobilized, wherein the immobilized antibody further binds a second antigen bearing a label, and wherein the first antigen and the second antigen are derived from a homologous source, the improvement comprising deriving the second antigen from a source that is heterologous to the source of the first antigen.

In particular, the present invention is directed to a method for detecting an antigen specific antibody in a test sample comprising the steps of:

(a) immobilizing a first recombinant derived antigen specific to the antibody to be detected on a solid phase;

(b) contacting the solid phase produced in step (a) with an aqueous phase test sample containing or suspected of containing the antigen specific antibody;

(c) contacting the solid phase produced in step (b) with an aqueous phase containing a second recombinant derived antigen having a label affixed thereto, the second recombinant derived antigen being derived from a source that is heterologous to the source of said first recombinant derived antigen;

(d) separating the aqueous phase from the solid phase;

(e) measuring the presence of the label on the solid phase or in the liquid phase to detect and/or titer the presence of antibody in the test sample.

This invention further relates to a modification of the described device and method wherein both the coated antigen and the labeled antigen, which are from heterologous sources, need not be identical so long as the antigens have at least one antigenic determinant ("epitope") in common.

DETAILED DESCRIPTION OF THE INVENTION

The present invention relates to a method of performing an immunoassay for the detection of antigen specific antibodies in a test sample comprising a biological fluid.

By "immunoassay" as used herein is meant a method for detecting or quantitating an analyte of interest by directly measuring the amount of analyte ultimately bound to a label. An immunoassay is to be distinguished from a competitive protein assay in which the detection or quantitation of an analyte is related to the amount of labeled analyte competitively displaced from binding sites by the unlabeled analyte from the biological fluid.

By "biological fluid" as used herein is meant fluids derived from mammalian organisms such as whole blood, serum, plasma, urine, saliva, cerebrospinal fluid (CSF), amniotic fluid, tissue extracts and dilutions or concentrates thereof.

The device and method of immunoassay described in the present invention utilize both a solid phase and a label.

By "solid phase" as used herein is meant any non-solution phase material having a surface to which antigen can be affixed by covalent or non-covalent means. By affixation by covalent means is generally meant a means of affixation employing agents well-known in the art, such as by the use of (i) a cyanogen halide such as cyanogen bromide or (ii) glutaraldehyde. By affixation by non-covalent means is meant absorption or adsorption. Although it is within the scope of this invention to affix antigen by any non-covalent means, it is particularly preferred that the antigens of this invention be affixed to the solid phase of this invention by adsorption.

Illustrative of the solid phase of this invention are microparticles or beads of plastic, glass, or latex; test tubes of plastic or glass; cellulose and modified cellulose materials; glass or plastic fibrous materials; and the like. Illustrative of a plastic particularly suited as a solid phase material is polystyrene. Most preferredly, the solid phase is a polystyrene bead of sufficient size to fit in a reaction vessel, such as a test tube, microtiter well, or the like.

By "label" as used herein is meant any molecule or elemental isotope conjugated or bound to an antigen which is capable of producing a signal or which is capable of acting upon other molecules so as to produce a detectable species. Molecules which are "capable of producing a signal" are radioisotopes, such as $^{125}I$ and the like, and fluorescing molecules such as fluorescein, fluorescein analogues and derivatives, phycobiliprotein, unbelliferone, and umbelliferone analogues and derivatives. Molecules which are "capable of acting upon other molecules so as to produce a detectable signal" are the various enzymes known in the art which can either act directly upon a substrate or which may be coupled to other enzymes acting upon substrate to produce a chromophore or fluorescent molecule capable of detection either by instrument or visually.

By "chromophore" is meant a molecule having an absorption peak wherein the absorption peak occurs between about 340 nm to about 720 nm in the electromagnetic spectrum.

The preferred labels in this invention are the radioisotopes and enzymes. Especially preferred as a label is the radioisotope $^{125}I$.

By "probe" as used herein is meant a heterologous antigen, epitope or hapten, which is capable of being bound by antibody and to which a label has been covalently affixed by chemical or recombinant technology.

The immunoassay of the present invention can be performed in either a two-step or one-step procedure. In the two-step procedure, the first step comprises incubating a solid phase, which is coated with antigen from one source, with an aqueous phase test sample containing an unknown amount of the antibody to the antigen. Antibody to the antigen binds to coated antigen via one of its two binding sites, thereby becoming part of the solid phase ("solid phase antibody").

In the second step, the solid phase is first washed and then incubated with an aqueous phase containing labeled antigen, wherein the labeled antigen is from a source that is heterologous to the antigen coating the solid phase. During incubation, the labeled antigen (probe) from the heterologous source is captured from the aqueous phase by the solid phase antibody via the antibody's second antigen bind site.

Thereafter, the solid phase and unreacted reagents in the aqueous phase are separated. The presence of the label is optionally measured either in the solid phase or aqueous phase. The amount of antibody present in the test sample is mathematically related both to the amount of labeled antigen bound to the solid phase and to the amount of labeled antigen remaining in the aqueous phase. However, it is preferred to utilize the solid phase to determine the presence or amount of antibody in the test sample.

By "aqueous phase" as used herein is meant any liquid phase having from about 50% to about 100% water with the balance an organic liquid which does not adversely affect the binding of antigen to the bead or the antibody to the antigen. Such organic liquids include the low molecular weight alcohols, the polyethylene glycols, dimethylsulfoxide and the like.

The one-step procedure comprises simultaneously adding to a bead coated with antigen from one source, a test sample and labeled antigen from a heterologous antigen source. After a measured incubation period, the solid phase and unreacted reagents are separated and the label is measured as previously described for the two-step procedure.

In this assay, only antigen, which is specific for the antibody to be detected, will react to form an antigen-antibody-antigen sandwich thereby providing the immunoassay with a high degree of specificity. More particularly, the overall sandwich consists of solid phase-antigen-antibody-heterologous antigen-label.

The immunoassay device and method of the present invention is more specific than prior art type sandwich immunoassays in which the antigen for the solid phase and the probe (labeled antigen) are derived from the same source. In particular, antigen purified from a single source (organism) will contain trace contaminants from that organism which during processing will become bound or incorporated into or onto the immunoassay's solid phase. These solid phase contaminants are then capable of binding antibody to the contaminants which may be present in the test sample. However, when the same antigen is purified from a heterologous source (organism), and labeled as the probe, it will contain a different set of contaminants. Accordingly, when the heterologous antigen and its set of contaminants are labeled, antibody to the first contaminants, which is bound to the solid phase, will not find a labeled contaminant with which to bind as to produce a false positive. Only the antigen itself, which is common to both organisms, is capable of forming the antigen-antibody-heterologous antigen sandwich. Thus, only labeled antigen is capable of binding to solid phase antibody to produce a true positive result. Accordingly, it is this feature which confers a specificity to this method of immunoassay which is not otherwise achievable by the methods of immunoassay, described in the prior art.

Although the device and process described in this invention can be used to detect and/or titer any antibody in a biological fluid, a preferred use of this invention is in the detection or titering of either antibody to the p41 envelope antigen of HTLV III, antibody to hepatitis B surface antigen (HbsAg), or antibody to hepatitis B core antigen (HBcAg). Most preferably, the device and method of this invention is used to detect and/or titer antibody to the p41 antigen of HTLV III, which is believed to be the first and most universal antibody response in individuals infected by HTLV III.

The preparation of antigens, such as the p41 envelope antigen of HTLV III. is well known in the art. For example, one could disrupt a virus, such as HTLV III, and purify the p41 antigen via multiple chromatographic separations, isoelectric focusing, and affinity chromatography.

A more preferred method of preparation of a pure antigen. such as the p41 antigen, is via recombinant DNA techniques. The first stage in such techniques would be to obtain a length of cDNA coding for the desired p41 antigen. One way to do this would be to isolate mRNA from the HTLV III virus and, with the in vitro use of reverse transcriptase, produce cDNA coding for the desired p41 antigen.

Alternatively, the DNA may be chemically synthesized. A number of oligonucleotides may be produced, from which the desired cDNA can be synthetically built up by the use of DNA polymerase and DNA ligase. Restriction endonuclease digestion of either end can leave appropriate cohesive restriction sites for insertion into a plasmid.

The synthetic DNA or cDNA disclosed above can be terminally tailed (have cohesive ends provided) either by a restriction endonuclease or it may be terminally tailed by the use of the appropriate nucleotide, such as oligo-dC, and terminal transferase.

Whichever tailing method is chosen, a plasmid, such as pUC-9 (Pharmacia, Piscataway, N.J.), can then be taken and cleaved at a single site by a restriction endonuclease, such as PstI (Sigma Chemical Co., St. Louis, Mo.). Cleaved pUC-9 can be oligo-dG tailed to complement an oligo-dC tail piece of DNA coding for the desired peptide. The cleaved plasmid and the DNA coding for the antigen can be annealed and ligated. Host cells such as *Escherichia coli* (*E. coli*) can be transformed by incubation with the appropriate recombinant plasmid, into p41 antigen producing cells. The transformed *E. coli* host cells may then be cultured under appropriate conditions to express the p41 antigen in quantity. Purification of the p41 protein is accomplished as described in Example 6. The various manipulations involving nucleic acids are described in Miniatis, et al., *Molecular Cloning*, Cold Spring Harbor Laboratory, 3–17 (1982).

Similarly, any other protein or glycoprotein, for which a cDNA fragment is obtained, can be expressed utilizing the technique described above. However, especially preferred as proteins and glycoproteins providing the antigens of this invention are the following: the p41 envelope protein, the p24 core protein and the gp120 surface glycoprotein of HTLV III (also known as HIV); and the various antigens of the hepatitis B virus (HBV), such as surface antigen (HBsAg), core antigen (HBcAg), and the e-antigen (HBeAg). Purification of these proteins is accomplished using the techniques described in Example 6.

Similarly, utilizing the techniques described above, a yeast may be transformed into an antigen producing organism by providing it with an appropriate recombinant plasmid containing the DNA coating for the antigen of interest, such as p41, thereby providing the heterologous organism of this invention.

Examples of heterologous organisms suited for antigen production include bacteria, such as *Escherichia coli* and *Bacillus megaterium*, yeast, mouse cell lines, and human cells lines such as H9 (Messing et al., *Methods Enzymol.*, 101, 20–78 (1983)). Although, antigens produced by any two heterologous organisms will provide satisfactory results in this invention, yeast is particularly preferred as the organism producing the p41 antigen for coating on or to the plastic bead; and *E. coli* is the preferred organism for producing the p41 antigen for conjugation to a label.

It is also within the scope of this invention that the antigen coated on the solid phase and the antigen bound to the label not be completely identical so long as both antigens have at least one antigenic determinant ("epitope") in common which can give rise to the highly specific antigen-antibody-antigen sandwich of the present invention.

For example, in the case of the p41 antigen, the complete p41 antigen may be cloned and expressed in an organism so as to contain the immunodominant domain of p41 and its hydrophobic carboxyl terminal domain. The hydrophobic carboxyl terminal domain aids in its ability to adhere to the solid phase. The p41 antigen for use in the label may consist only of the amino terminal half of the p41 molecule, which lacks the hydrophobic region but contains the immunodominant domain, thereby permitting an antibody to bind to both p41 antigens and form the high specific antigen-antibody-antigen sandwich of this invention.

It is also within the scope of this invention that epitopes of the antigen in the probe (i.e. epitope conjugated to the label) be optionally expressed by recombinant technology. Similarly it is within the scope of this invention that recombinant technology be employed to express an epitope according to this invention wherein the epitope is expressed with an enzymatic label already affixed to it.

Other applications of this invention include use of the same configuration to make a combination assay in which 2 or more antigens are coated onto a solid phase and 2 or more antigens from heterologous sources are used as a probe so that multiple antibodies may be detected simultaneously.

Furthermore, this invention may be applied to determine whether a sample contains antibody to a conserved region of a highly variable protein. For example, gp120 from HTLV III could be purified from two distantly related HTLV III strains, gp120 from one strain being then used to coat the solid phase and gp120 from the other strain used as a probe, i.e., labeled antigen.

Thus, there are many advantages to the immunoassay method and device described in the present invention. In particular, the immunoassay described in the present invention is more specific than the prior art immunoassays which do not employ the heterologous antigen sources. Moreover, the described immunoassay method and device for detecting antibody to HTLV III is substantially more specific than the prior art immunoassay for human anti-HTLV III which uses relatively nonspecific probes such as labeled goat anti-human IgG, IgM or IgA. Further, the assay is simple to perform. Additionally, the anti-HTLV III immunoassay which is described herein, does not require the 1:100 or 1:400 dilutions of test sample required by the prior art.

The following examples are intended to illustrate the invention and not to limit its scope or spirit, since based upon this disclosure many modifications in methods and material will be obvious to those skilled in the art.

DESCRIPTION OF THE PREFERRED EMBODIMENT

EXAMPLE 1

Isotopic Two-Step direct Immunoassay Method For Anti-p41

This example illustrates a two-step direct immunoassay for the detection of anti-p41 utilizing a radioactive label, carried out in accordance with the invention. The radioactively labeled antigen is prepared according to the method of Greenwood, et al., *J. Biochem.*, 89:114–123 (1963).

A polystyrene bead (¼ inch) is coated with p41 antigen expressed in and derived from yeast in phosphate buffered saline, 0.5 μg/ml pH 7.0, 2 hrs at 45° C. Next, 200 μl human serum sample containing an unknown amount of anti-p41 is added to the bead and incubated on a level surface for 2 hours at 40° C. The bead is washed three times with 4 ml deionized water. Then, 200 μl p41 antigen derived from yeast labeled with $^{125}$I is added to the washed bead and incubated for one hour at 40° C. The bead is washed three times with 5 ml deionized water and transferred to a test tube for radioactivity counting on a gamma scintillation counter such as an ANSR gamma counter made by Abbott Laboratories, North Chicago, Ill. The greater the amount of anti-p41 present in the serum sample, the greater the amount of radioactivity detected.

This same immunoassay can also be performed utilizing a polystyrene bead coated with p41 derived from *E. coli*. Using this method, p41 derived from yeast labeled with $^{125}$I is used. Both assays perform equally well for the detection of anti-p41.

EXAMPLE 2

Enzymatic Two-Step Direct Immunoassay Method For Anti-p41

This example is a two-step direct immunoassay for anti-p41 utilizing an enzyme. Horseradish peroxidase (HRPO) labeled antigen is prepared according to the method of Nakane, et al., *J. Histochem. Cytochem.*, 22:1084–1091 (1974) or p41 is biotinylated (Hofmann, K. et al., (1982) Biochem.) and reacted with rabbit anti-biotin labeled with HRPO.

A polystyrene bead is coated with p41 antigen (yeast) as described in Example 1. To the bead is added 200 μl of human serum sample and the combined solid and aqueous phase is incubated on a level surface for 2 hours at 40° C. The bead is then washed three times with 5 ml deionized water. Next, 200 μl of p41 antigen (*E. coli*) labeled with horseradish peroxidase either directly or by use of a biotin/anti-biotin system is added to the bead and incubated for 1 hour at approximately 40° C. The bead is washed three times with 5 ml deionized water and transferred to a test tube for development of color. To the bead in the test tube is added 300 μl of o-phenylenediamine (OPD) substrate solution (comprising a 12.8 mg tablet of o-phenylenediamine.2HCl, diluted in 5 ml of 0.1M citrate-phosphate buffer, pH 5.5–6.0 containing 0.02% hydrogen peroxide) and the combination is incubated for 30 minutes at room temperature. Thereafter, 1.0 ml of 1N sulfuric acid is added to the tube. The color produced is read on a spectrophotometer with absorbance determined at a wavelength of approximately 492 nm. The greater the amount of anti-p41 in the sample, the higher the absorbance measured.

As indicated in the isotopic immunoassay of Example 1, the source of p41 selected for the bead in Example 2 can be reversed with the source of p41 selected to be labeled, so long as one source of p41 is heterologous to the other.

EXAMPLE 3

One-Step Assay for Anti-p41

This example demonstrates a one-step assay according to the invention, utilizing either a radioactive or enzyme label.

A polystyrene bead is coated with p41 (yeast) as set forth in Example 1. To the bead in a reaction vessel is added 100 μl of human serum sample and 100 μl of p41 (*E. coli*) labeled with either $^{125}$I or horseradish peroxidase and incubation is allowed to continue for about 2 hours at 40° C. The bead is then washed three times with 5 ml deionized water and transferred to a test tube for either the counting of radioactivity (as in Example 1), or the development of color and the measurement of absorbance at 492 nm (as in Example 2).

EXAMPLE 4

Two-step Direct Immunoassay Method For Anti-HBsAg

This method details a two-step direct immunoassay method for antibody to hepatitis B surface antigen. In this method, horseradish peroxidase (HRPO) was prepared by the method of Nakane, et al., *J. Histochem. Cytochem.*, 22: 1084–1091 (1974). Alternatively, HBsAg can be biotinylated by the method of Ngo, et al., and reacted with either anti-biotin (mouse monoclonal or rabbit polyclonal) or avidin to which is labeled HRPO. See: Ngo. et al., *J. Appl. Biochem. Biotech.*, 7, 443–454 (1982). HRPO labeled avidin is commercially available from Sigma Chemical Co., St. Louis, Mo.

This procedure was performed according to Example 2 except that HBsAg derived from human plasma was used to coat the bead and recombinant derived HBsAg from transfected mouse L cells was used as the probe i.e., conjugated to the HRPO label.

The reaction curve presented below was typical of results obtained by this method.

| Anti-HBsAg Conc. | Absorbance at 492 nn |
|---|---|
| Negative Control | 0.022 |
| Positive Control | 1.536 |
| 150 mIU/ml | 1.588 |
| 75 mIU/ml | 0.832 |
| 40 mIU/ml | 0.599 |
| 15 mIU/ml | 0.220 |
| 8 mIU/ml | 0.141 |

-continued

| Anti-HBsAg Conc. | Absorbance at 492 nn |
|---|---|
| 4 mIU/ml | 0.082 |

EXAMPLE 5

Qualitative Three Step Immunoassay For Anti-p41

This example describes a three step direct immunoassay method for anti-p41 in which microparticles coated with recombinant p41 expressed in and derived from *Bacillus megaterium* (*B. meg.*) are deposited on a filter and used as the solid phase. See, U.S. Pat. No. 4,632,901 describing a solid phase comprising coated microparticles deposited on a filter.

In this method, 300 μl of a test sample is added to 200 μl of sample diluent, poured onto the filter which is situated over an absorbent pad and allowed to incubate for 3 minutes. The filter containing the microparticles over which the diluted sample passed is then reacted for 3 minutes with biotinylated p41 prepared by the procedure of Ngo, et al., *J. Appl. Biochem and Biotech.*, 7, 443-454, (1982). Thereafter, to the filter is added a solution containing either alkaline phosphate labeled antibodies to biotin or alkaline phosphate labeled avidin. After a 3 minute incubation, the filter is extensively washed with a buffered saline solution, pH 6.5-9.5, 0.9% NaCl. To the filter is then added a solution of substrate which is reacted upon by any immobilized alkaline phosphatase to produce a chromogen indicating the presence of antibody to p41 and hence exposure to the virus HTLV III.

Although any organic phosphate compound capable of producing a chromophore on hydrolysis by alkaline phosphatase is suitable as a substrate, preferred substrates are the substituted phenyl, naphthyl and indole phosphates. Especially preferred as substrates for the alkaline phosphatase label is 5-bromo-4-chloro-3-indolyl phosphate or 3-indoxyl phosphate and analogues or derivatives thereof.

EXAMPLE 6

Purification And Characterization p41 and p24 Antigens Of HTLV III

The HTLV III p41 recombinant protein produced in *E. coli* is purified using affinity column and ion exchange chromatography. The bacterial lysate supernatant is passed over an affinity column composed of Sepharose 4B beads bound with monoclonal anti-HLTV III-p41. The column is washed with a buffer of 0.5% TRITON X-100 and the bound HTLV III p41 was eluted with the same buffer containing 5M NaI. The eluted protein solution was dialyzed extensively to remove NaI and mixed 1:1 with an ethanolamine buffer containing 0.1% Tween 20 and 7M urea (Buffer A) and applied to a DEAE anion exchange column. The column was extensively washed in Buffer A, then bound protein was eluted using a 100-500 mM NaCl gradient in Buffer A. Peak fractions of p41 activity were pooled and dialyzed to remove urea.

Similarly, the p24 recombinant produced in *E. coli* is purified by passage of bacterial lysate supernatant over an affinity column composed of Sepharose 4B beads bound with monoclonal anti-HTLV III-p24. The column is washed with a buffer containing 0.1% TRITON X-100, and the bound p24 is eluted with the same buffer containing 4M guanidine hydrochloride (GuHCl). The eluted protein solution is dialyzed extensively, then reapplied to a second affinity column and eluted as described above. Peak fractions of p24 are pooled and dialyzed to remove GuHCl.

To further characterize the recombinant proteins, the purified p24 core or p41 envelope antigens are subjected to sodium dodecylsulfate polyacrylamide gel electrophoresis (SDS PAGE) and Western Blot analysis according to Schupbach et al., *Science*, 224, 503-505 (1984).

What is claimed is:

1. In the method of performing a sandwich immunoassay for detecting antibody to a specific antigen in a test sample wherein a first antigen specific to the antibody to be detected is immobilized on a solid phase, wherein the antibody to be detected in the test sample binds to the first antigen thereby becoming immobilized, wherein said immobilized antibody further binds a second antigen bearing a label, and wherein the first antigen and the second antigen are derived from a homologous source; the improvement comprising deriving the second antigen from a source that is heterologous to the source of the first antigen.

2. A method for detecting an antigen specific antibody in a test sample comprising the steps of:
   (a) immobilizing a first recombinant derived antigen specific to the antibody to be detected on a solid phase;
   (b) contacting the solid phase produced in step (a) with an aqueous phase test sample containing or suspected of containing the antigen specific antibody;
   (c) contacting the solid phase produced in step (b) with an aqueous phase containing a second recombinant derived antigen having a label affixed thereto, the second recombinant derived antigen being derived from a source that is heterologous to the source of said first recombinant derived antigen;
   (d) separating the aqueous phase from the solid phase;
   (e) measuring the presence of the label on the solid phase or in the liquid phase to detect and/or titer the presence of antibody in the test sample.

3. The method of claim 2 wherein the label is an enzyme or radioisotope.

4. The method of claim 2 wherein both the first and second recombinant derived antigens simultaneously possess at least one antigenic determinant in common, said antigenic determinant being a member of the group consisting of the p24 antigen of HTLV III, the p41 antigen of HTLV III, the gp120 antigen of HTLV III, HBsAg, HBcAg, HBeAg, with the proviso that the first and second recombinant derived antigens have sufficient antigenic determinants in common to permit cross-linking by antigen specific antibody in the test sample.

5. The method of claim 2 wherein steps (b) and (c) are performed simultaneously.

6. The immunoassay of claim 2 wherein the solid phase is a polystyrene bead.

7. A method for detecting antibody to the p41 antigen of HTLV III which may be present in a human serum sample, comprising the steps of:
   a. coating a polystyrene bead with purified p41 antigen from yeast;
   b. adding the human serum sample to the coated bead;

c. incubating for about 2 hours at approximately 40° C.;

d. washing the bead with deionized water;

e. adding to the bead a purified p41 antigen of HTLV III labeled with a detectable label which antigen simultaneously possesses at least one antigenic determinant in common with said antigen of step (a) wherein said antigen is derived from an organism heterologous from that used to produce the p41 antigen of HTLV III coated on the bead; said antigen having sufficient antigenic determinants in common with the antigen of step (a), thereby permitting cross-linking by an antibody to p41 in the human serum sample;

f. incubating for about 1 hour at approximately 40° C.;

g. washing the bead with deionized water;

h. separating unreacted reagents from the bead; and i. measuring the presence of the labeled p41 antigen to HTLV III on the bead.

8. The method of claim 7 wherein the p41 antigen of step (a) is produced in yeast, and the labeled p41 antigen of step (e) is produced in $E.\ coli$.

9. The method of claim 7 wherein the p41 antigen of step (e) is produced in mouse cells.

10. The method of claim 7 wherein the detectable label is $^{125}$I.

11. The method of claim 7 wherein the detectable label is horseradish peroxidase.

12. The method of claim 7 wherein step (c) comprises incubating for 2 hours at 40° C., and step (f) comprises incubating for 1 hour at 40° C.

13. A method for detecting an antigen specific antibody which may be present in a test sample comprising the steps of:

(a) immobilizing a first antigen specific to the antibody to be detected on a solid phase;

(b) contacting the solid phase produced in step (a) with an aqueous phase test sample containing or suspected of containing the antigen specific antibody;

(c) contacting the solid phase produced in step (b) with an aqueous phase containing a second antigen having a label affixed thereto, said second antigen being derived from a source that is heterologous to the source of said first antigen;

(d) separating the aqueous phase form the solid phase;

(e) measuring the presence of the label on the solid phase or in the liquid phase to detect and/or titer the presence of antibody in the test sample.

14. A method for detecting an antigen specific antibody in a test sample comprising:

(a) contacting an aqueous phase test sample containing or suspected of containing the antigen specific antibody with a solid phase upon which a first recombinant derived antigen specific to the antibody has been immobilized;

(b) contacting said solid phase of step (a) with an aqueous phase containing a second recombinant derived antigen having a label affixed thereto, said second derived antigen being derived from a source that is heterologous to the source of said first recombinant derived antigen;

(c) separating the aqueous phase from the solid phase; and (d) measuring the presence of the label on the solid phase or in the liquid phase to detect and/or tier the presence of antibody in the test sample.

15. The method of claim 14 wherein both the first and second recombinant derived antigens simultaneously possess at least one antigenic determinant in common, said antigenic determinant being a member of the group consisting of the p24 antigen of HTLV III, the p41 antigen of HTLV III, the gp120 antigen of HTLV III, HBsAg, HBcAg and HBeAg, with the proviso that the first and second recombinant derived antigens have sufficient antigenic determinants in common to permit cross-linking by antigen specific antibody in the test sample.

16. The method of claim 14 wherein step (a) and step (b) are performed simultaneously.

17. The method of claim 14 wherein said label is selected from the group consisting of an enzyme, a radioisotope, and a fluorescent marker.

18. The method of claim 14 wherein the solid phase is selected from the group consisting of a microparticle, a bead, a test tube, modified cellulose material, glass fibrous matrices and plastic fibrous matrices.

19. A method for detecting an antigen specific antibody in a test sample comprising:

(a) contacting an aqueous phase test sample containing or suspected of containing the antigen specific antibody with a solid phase upon which a first antigen specific to the antibody has been immobilized;

(b) contacting said solid phase of step (a) with an aqueous phase containing a second antigen having a label affixed thereto, said second derived antigen being derived from a source that is heterologous to the source of said first derived antigen;

(c) separating the aqueous phase from the solid phase; and (d) measuring the presence of the label on the solid phase or in the liquid phase to detect and/or titer the presence of antibody in the test sample.

20. The method of claim 19 wherein both the first and second antigens simultaneously possess at least one antigenic determinant in common, said antigenic determinant being a member of the group consisting of the p24 antigen of HTLV III, the p41 antigen of HTLV III, the gp120 antigen of HTLV III, HBsAg, HBcAg and HBeAg, with the proviso that the first and second antigens have sufficient antigenic determinants in common to permit cross-linking by antigen specific antibody in the test sample.

21. The method of claim 19 wherein step (a) and step (b) are performed simultaneously.

22. The method of claim 19 wherein said label is selected from the group consisting of an enzyme, a radioisotope, and a fluorescent marker.

23. The method of claim 19 wherein the solid phase is selected from the group consisting of a microparticle, a bead, a test tube, modified cellulose material, glass fibrous matrices and plastic fibrous matrices.

* * * * *